US012629432B2

(12) United States Patent
Ulmert et al.

(10) Patent No.: US 12,629,432 B2
(45) Date of Patent: May 19, 2026

(54) IMMUNOTHERANOSTIC AGENT TARGETING MESENCHYMAL STEM CELL-DERIVED CANCER CELLS AND MESENCHYMAL STEM CELL ASSOCIATED DISEASE

(71) Applicant: Lantheus Omega, LLC, Bedford, MA (US)

(72) Inventors: Hans David Ulmert, Santa Monica, CA (US); Norbert Peekhaus, Los Angeles, CA (US); Liqun Mao, Los Angeles, CA (US); Robert D. Damoiseaux, Beverly Hills, CA (US); Claire Storey, Los Angeles, CA (US)

(73) Assignee: Lantheus Omega, LLC, Bedford, MA (US)

( * ) Notice: Subject to any disclaimer, the term of this patent is extended or adjusted under 35 U.S.C. 154(b) by 635 days.

(21) Appl. No.: 17/915,377

(22) PCT Filed: Mar. 31, 2021

(86) PCT No.: PCT/US2021/025054
§ 371 (c)(1),
(2) Date: Sep. 28, 2022

(87) PCT Pub. No.: WO2021/202642
PCT Pub. Date: Oct. 7, 2021

(65) Prior Publication Data
US 2023/0133775 A1    May 4, 2023

Related U.S. Application Data

(60) Provisional application No. 63/003,598, filed on Apr. 1, 2020.

(51) Int. Cl.
*A61K 51/10*        (2006.01)

(52) U.S. Cl.
CPC ...... *A61K 51/1027* (2013.01); *A61K 51/1093* (2013.01)

(58) Field of Classification Search
USPC ...................................................... 424/1.49
See application file for complete search history.

(56) References Cited

U.S. PATENT DOCUMENTS

| | | | |
|---|---|---|---|
| 9,815,898 B2 | 11/2017 | Freeman et al. | |
| 2018/0079816 A1 | 3/2018 | Chang et al. | |

FOREIGN PATENT DOCUMENTS

| | | |
|---|---|---|
| CN | 109219618 A | 1/2019 |
| JP | A 2016-056165 | 4/2016 |
| JP | 2018-162306 | 10/2018 |
| WO | WO2013149159 | 10/2013 |
| WO | WO 2017/095808 | 6/2017 |
| WO | WO2017095805 | 6/2017 |
| WO | WO-2017125831 A1 | 7/2017 |
| WO | WO2018083087 | 5/2018 |
| WO | WO2018227018 | 12/2018 |
| WO | WO2019173692 | 9/2019 |
| WO | WO 2019-195278 | 10/2019 |
| WO | WO 2019-203191 | 10/2019 |
| WO | WO-2021202642 A2 | 10/2021 |

OTHER PUBLICATIONS

International Search Report and Written Opinion, mailed Oct. 4, 2021, from corresponding International Application No. PCT/US2021/025054.
Labrijn et al., "Bispecific antibodies: a mechanistic review of the pipeline", Nature Review Drug Discovery, 2019; 18:585-608.
Brinkmann et al., "The making of bispecific antibodies", MABS, Feb./Mar. 2017; 9(2):182-212.
Sedykh et al., "Bispecific antibodies: design, therapy, perspectives", Drug Design, Development and Therapy, Jan. 22, 2018; 12:195-208.
Wu et al., "Building blocks for bispecific and trispecific antibodies", Methods, Feb. 1, 2019; 154:3-9.
Runcie et al., "Bi-specific and tri-specific antibodies—the next big thing in solid tumor therapeutics", Molecular Medicine, 2018; 24:50, 15 pages.
Partial Supplementary European Search Report, dated Nov. 7, 2024, from corresponding European Patent Application No. 21780744.5.
Extended European Search Report, dated Jan. 28, 2025, from corresponding European Patent Application No. 21780744.5.
Purcell et al., "LRRC15 Is a Novel Mesenchymal Protein and Stromal Target for Antibody-Drug Conjugates", Cancer Research, Jul. 15, 2018; 78(14):4059-4072.
Ben-Ami et al., "LRRC15 Targeting in Soft-Tissue Sarcomas: Biological and Clinical Implications", Cancer, Mar. 23, 2020; 12(3): 757; doi: 10.3390/cancers12030757.
Pathoulas, "Investigating the Therapeutic Potential of Targeting LRRC15 in Endometrial Cancer", Oct. 5, 2019; All College Thesis Program, 2016-2019.60, Retrieved from the Internet: https://digitalcommons.csbsju.edu/honors_thesis/60.
Demetri et al., "First-in-human phase 1 study of ABBV-085, an antibody-drug conjugate (ADC) targeting LRRC15, in sarcomas and other advanced solid tumors", Journal of Clinical Oncology, May 20, 2019; 37(15_suppl):3004, abstract.
(Continued)

*Primary Examiner* — Walter E Webb

(74) *Attorney, Agent, or Firm* — Sterne, Kessler, Goldstein & Fox P.L.L.C.

(57) ABSTRACT

The present disclosure provides a radiotheranostic agent targeting LRRC15 expressed on cells derived from or associated with mesenchymal stem cells. The LRRC15 targeting agent would significantly improve diagnosis and treatment of a broad range of diseases and malignancies. In one embodiment, the LRRC15 targeting agent is a humanized monoclonal antibody (DUNP19) that has high binding affinity to LRRC15 and is internalized by cells expressing LRRC15.

22 Claims, 7 Drawing Sheets

Specification includes a Sequence Listing.

(56)           References Cited

OTHER PUBLICATIONS

Hingorani et al., "ABBV-085, Antibody-Drug Conjugate Targeting LRRC15, Is Effective in Osteosarcoma: A Report by the Pediatric Preclinical Testing Consortium", Molecular Cancer Therapeutics, Mar. 2021; 20(3):535-540.

Second Amended Complaint and Demand for Jury Trial, Case No. 2:24-cv-03961-JFW (PDx), *Agensys, Inc. and Astellas Pharma, Inc.*, Plaintiffs, v. *Hans David Ulmert and Norbert Peekhaus*, Defendants, Document 83, Filed Oct. 31, 2024, 38 pages.

Answer of Defendant Norbert Peekhaus to Second Amended Complaint, Case No. 2:24-cv-03961-JFW (PDx), *Agensys, Inc. and Astellas Pharma, Inc.*, Plaintiffs, v. *Hans David Ulmert and Norbert Peekhaus*, Defendants, Document 91, Filed Nov. 14, 2024, 37 pages.

Defendant Hans David Ulmert's Answer to Second Amended Complaint, Case No. 2:24-cv-03961-JFW (PDx), *Agensys, Inc. and Astellas Pharma, Inc.*, Plaintiffs, v. *Hans David Ulmert and Norbert Peekhaus*, Defendants, Document 106, Filed Dec. 19, 2024, 27 pages.

SEQUENCE LISTING

<160> NUMBER OF SEQ ID NOS: 4

<210> SEQ ID NO 1
<211> LENGTH: 120
<212> TYPE: PRT
<213> ORGANISM: Artificial
<220> FEATURE:
<223> OTHER INFORMATION: Humanized heavy chain variable sequence that
      binds LRRC15

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Asp Gly Thr Asn Tyr Ala Gln Asn Phe
    50                  55                  60

Leu Gly Arg Val Thr Met Thr Arg Asp Thr Ser Ile Ser Thr Ala Tyr
65                  70                  75                  80

Met Glu Leu Ser Arg Leu Arg Ser Asp Asp Ser Ala Val Tyr His Cys
                85                  90                  95

Val Arg Glu Gly Arg Tyr Ser Thr Ser Pro Phe Asp Tyr Trp Gly Gln
            100                 105                 110

Gly Thr Leu Val Thr Val Ser Ser
        115                 120

<210> SEQ ID NO 2
<211> LENGTH: 114
<212> TYPE: PRT
<213> ORGANISM: Artificial
<220> FEATURE:
<223> OTHER INFORMATION: Humanized light chain variable seqeunce that
      binds LRRC15

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Arg Asn Tyr Leu Ala Trp Tyr Gln Gln Lys Pro Gly Gln
        35                  40                  45

Pro Pro Lys Leu Phe Ile Tyr Trp Ser Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gln Gly Thr Lys Leu Glu Ile
            100                 105                 110

Lys Arg

<210> SEQ ID NO 3
<211> LENGTH: 120
<212> TYPE: PRT
<213> ORGANISM: Artificial
<220> FEATURE:
<223> OTHER INFORMATION: Human heavy chain variable seqeunce that binds
      TGFb -continued

```
<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Ser Asn
            20                  25                  30

Val Ile Ser Trp Val Arg Gln Ala Pro Gly Gln Gly Leu Glu Trp Met
        35                  40                  45

Gly Gly Val Ile Pro Ile Val Asp Ile Ala Asn Tyr Ala Gln Arg Phe
    50                  55                  60

Lys Gly Arg Val Thr Ile Thr Ala Asp Glu Ser Thr Ser Thr Thr Tyr
65                  70                  75                  80

Met Glu Leu Ser Ser Leu Arg Ser Glu Asp Thr Ala Val Tyr Tyr Cys
                85                  90                  95

Ala Ser Thr Leu Gly Leu Val Leu Asp Ala Met Asp Tyr Trp Gly Gln
            100                 105                 110

Gly Thr Leu Val Thr Val Ser Ser
        115                 120

<210> SEQ ID NO 4
<211> LENGTH: 108
<212> TYPE: PRT
<213> ORGANISM: Artificial
<220> FEATURE:
<223> OTHER INFORMATION: Human light chain variable seqeunce that binds
      TGFb

<400> SEQUENCE: 4

Glu Thr Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Pro Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Asp Ser Pro
                85                  90                  95

Ile Thr Phe Gly Gln Gly Thr Arg Leu Glu Ile Lys
            100                 105
```

IMMUNOTHERANOSTIC AGENT TARGETING MESENCHYMAL STEM CELL-DERIVED CANCER CELLS AND MESENCHYMAL STEM CELL ASSOCIATED DISEASE

CROSS-REFERENCE TO RELATED APPLICATION

This application is a National Phase Application of PCT International Application No. PCT/US2021/025054, International Filing Date Mar. 31, 2021, which claims priority to U.S. provisional patent application Ser. No. 63/003,598, filed Apr. 1, 2020, the entire contents of which are incorporated herein by reference.

FIELD OF THE INVENTION

The present disclosure relates generally to the field of disease imaging and therapy. In one embodiment, the present disclosure provides radiotheranostic agents that target LRRC15 expressed on cells derived from mesenchymal stem cells.

BACKGROUND OF THE INVENTION

Recent breakthroughs in immunobiotechnology have led to exciting therapeutic technologies and platforms using antibodies in the form of single-chain variable fragments, such as bispecific T-cell engagers (BiTE) and chimeric antigen receptors (CAR). However, most of these are only applicable to treat a limited number of solid tumors. The main factor contributing to therapeutic inefficacy and resistance is the tumor stromal compartment's ability to decrease infiltration of activated effector cells to the tumor bed. In addition, stromal cells actively orchestrate resistance through a myriad of other processes such as immune cell regulation, metabolic reprogramming, and hypoxia. The tumor stroma is comprised of a large array of epithelial, fibroblast, endothelial and inflammatory cell populations that coordinate together to regulate tumor growth and progression. Of these, cancer-associated fibroblasts (CAFs) are a unique cellular subset within the stroma due to their complex interaction with cancer cells. CAFs are a heterogeneous cell population with high degrees of cellular plasticity thought to arise from numerous cell types including resident fibroblasts, endothelial cells, cells undergoing epithelial-to-mesenchymal transition (EMT), and mesenchymal stem cells. This is a rapidly evolving area of tumor biology and many outstanding questions still remain regarding the origin, prevalence, and biological function of CAF populations across tumor types. Development of pharmaceuticals abating tumor specific immunosuppression have been focused on identifying targets that are specifically associated with cancer stroma, and the most coveted are plasma membrane proteins specific to CAFs. An absolute majority of these efforts have been targeting fibroblast activated protein a (FAP), a membrane bound serine protease overexpressed by CAFs. However, FAP is also expressed by normal tissues and healthy activated fibroblasts during wound healing, such as the activation of myofibroblasts post myocardial infarction. FAP-targeted therapeutic approaches (including antibody-drug conjugates, CAR-T cells and enzyme-inhibitors) have failed resulting in adverse effects or lack of efficacy due to low tumor specificity.

An alternative approach to pharmacologically regulate the immunosuppressive effects of the tumor stroma has been to target specific cytokines or regulatory pathway receptors. One of the leading endeavors is to attenuate the TGF-β pathway, which supports the evasion of cancer cells from immune surveillance and contributes to the subversion of the immune system from acting as an extrinsic tumor suppressor to a promoter of malignant growth and invasiveness. Along with numerous effects on neoplastic cells and tumor stroma, multipronged effects of TGF-β on immune cells shape the cancer microenvironment. For example, TGF-β activity dictates several aspects of T-cell fate decisions, NK cell functions and γδ Tregs. In addition, crosstalk between the canonical TGF-β signaling (SMADs) and several non-canonical pathways including MAPK, PI3K, WNT, HH, and NOTCH has been described. TGF-β inhibitors primarily exert their antitumor activity by affecting fibroblastic and endothelial cell growth as well as T-cell activation in the tumor microenvironment. Of the TGF-β pathway targeting drugs, small molecule TGF-β receptor inhibitors such as galunisertib (LY2157299) have shown the most promising results. Unfortunately, these inhibitors have been impeded by a narrow therapeutic window and toxic effects. Therefore, non-invasive biomarkers for patient selection and dose titration are currently needed in order to fully utilize TGF-β receptor inhibitors.

LRRC15 is a 581 amino acid type I membrane protein with an N-terminal transmembrane domain, 15 Leucine-rich repeats (LRRs), and a short C-terminal cytoplasmic tail. In general, proteins containing LRRs can have a wide variety of functions, including innate immunity, inflammation and nervous system development. The specific physiological function of LRRC15, a highly conserved molecule, is largely unknown and understudied but is likely impacting cell-matrix adhesion and cell migration. LRRC15 is governed by TGF-β, which has a leading role in tissue healing and immune regulation. The normal tissues that express LRRC15 are sites where TGF-β is reported to be present and where mesenchymal stem cells (MSCs) are known to reside, such as hair follicles, tonsil and sites of wound healing. Bone marrow and adipose derived MSCs, and to some extent umbilical cord derived MSCs, express LRRC15 under TGF-β stimulation. This feature of TGF-β governance is unique to LRRC15 compared to other mesenchymal associated markers such as FAP. Studies have shown that LRRC15 impacts osteogenesis through MSC differentiation and is a highly upregulated gene in focal erosions of rheumatic arthritis. Interestingly, LRRC15 expression also impedes adenovirus infection, supporting evidence for the protein's role as an important immune regulator.

LRRC15 is highly expressed on CAFs within the tumor stroma of a wide range of malignancies, as well as directly on cancer cells from a subset of mesenchymal tumors (e.g., sarcomas, glioblastoma multiforme). LRRC15⁺ CAFs emerge from a LRRC15⁺ fibroblast population as a result of TGF-β activity. Compared to FAP, LRRC15 has a significantly lower baseline expression and a higher differential RNA expression between cancer and adjacent normal tissues. In pancreatic adenocarcinoma (PDAC), LRRC15⁺ CAFs specifically surround tumor islets, while absent from normal pancreatic tissue. Preclinical and clinical studies evaluating genes associated with metastatic progression have identified LRRC15 to be among the top genes expressed in metastasis. LRRC15 has been shown to promote metastatic spread to bone and bowel in breast and ovarian cancer patients, respectively, while knockdown by siRNA significantly inhibited progression in preclinical models. Overexpression has also been associated with aggressive behavior in metastatic lesions of androgen independent metastatic prostate cancer. Importantly, analysis of tissues obtained from clinical trials show that high avidity of LRRC15+ CAFs is associated with resistance to immune checkpoint blockade.

There is an unmet need for non-invasive tools for identifying and treating molecular events and cellular phenotypes associated with immunotherapy resistance mechanisms. Specific eradication of the tumor stroma and pharmacological manipulation of the TGF-β pathway have both been exploited as monotherapies or in combination with immunotherapies to pharmacologically alleviate resistance. However, previous compounds designed to eliminate the stroma has been unsuccessful due to off-target expression, while compounds decreasing TGF-β activity are rarely applicable due to narrow therapeutic windows. Radiotheranostic compounds for molecularly precise eradication of tumor associated stroma and non-invasive imaging of downstream TGF-β activity could be particularly useful for curbing resistance mechanisms and ameliorating the therapeutic potential of modern immunotherapeutic compounds.

SUMMARY OF THE INVENTION

For decades, an absolute majority of cancer treatments have focused on targeting malignant cells without consideration of the tumor microenvironment (TME) and its unique role in tumor maintenance and progression. Aggressive malignancies such as pancreatic adenocarcinoma, glioblastoma multiforme (GBM) and osteosarcoma rely on the TME for tumor growth and maintenance, presenting a unique opportunity to target this critical interaction for therapeutic benefit. An integral component of the TME is the tumor stroma, a collection of fibroblasts, mesenchymal and epithelial cells vital to tumor progression. The present disclosure identified the tumor-specific membrane protein leucine-rich repeat containing 15 (LRRC15) as a highly upregulated protein across a wide range of malignancies of mesenchymal origin and in cancer-associated fibroblasts (CAFs). LRRC15 is thought to play a role in cell migration, cell adhesion and is highly associated with immunological response and resistance to immunotherapy.

The present disclosure presents an anti-LRRC15 antibody DUNP19, a humanized monoclonal antibody (mAb) that is rapidly internalized into target cells by binding to LRRC15 with high specificity and picomolar affinity (3.29e-10M). The DUNP19 mAb, or its derivatives, can be used as a molecular imaging tool and/or radiotherapeutic. Targeting tumor and stromal cells expressing LRRC15 via DUNP19 will generate novel radio-theranostic strategies for currently untreatable malignancies.

In one embodiment, there is provided a method for treating a disease having disease-associated tissue that is derived from or associated with mesenchymal stem cells. The method comprises the step of administering to a patient a binding moiety targeting LRRC15 expressed on cells in the disease-associated tissue, wherein the binding moiety is associated with a cytotoxic agent and the binding moiety is internalized by cells in the disease-associated tissue, thereby delivering the cytotoxic agent to the disease-associated tissue.

In another embodiment, there is provided a method for imaging disease-associated tissue that is derived from or associated with mesenchymal stem cells. The method comprises the step of administering to a patient a binding moiety targeting LRRC15 expressed on cells in the disease-associated tissue, wherein the binding moiety is associated with an imaging agent and the binding moiety is internalized by cells in the disease-associated tissue, thereby delivering the imaging agent to the disease-associated tissue.

In another embodiment, there is provided a method of selecting a patient for therapy with a molecule that inhibits TGF-β receptor signaling, wherein the patient has or is suspected of having a disease comprising disease-associated tissue that is derived from or associated with mesenchymal stem cells. The method comprises the steps of: a) administering to the patient a binding moiety targeting LRRC15 expressed on cells in the disease-associated tissue, wherein the binding moiety is associated with an imaging agent and the binding moiety is internalized by cells in said disease-associated tissue; b) determining a level of binding or internalization of the binding moiety; and c) when a patient is found to exhibit a higher level of binding or internalization of the binding moiety as compared to a control level in a control subject, the patient is selected for and treated with the therapy. In one embodiment, the control subject is a healthy subject or one without the disease in question.

In another embodiment, there is provided a method of determining a dose of a therapeutic agent for treating a disease in a patient, wherein the disease comprises disease-associated tissue that is derived from or associated with mesenchymal stem cells. The method comprises the steps of: a) administering to the patient a first dose or a prior dose of the therapeutic agent; b) administering to the patient a binding moiety targeting LRRC15 expressed on cells in the disease-associated tissue, the binding moiety is associated with an imaging agent and the binding moiety is internalized by cells in the disease-associated tissue; c) determining a level or rate of binding or internalization of the binding moiety; d) administering to the patient a follow-up dose of the therapeutic agent, wherein the follow-up dose is higher than the first or prior dose, and repeating steps b) and c); e) repeating step d) when the level or rate of binding or internalization of the binding moiety obtained after the follow-up dose is lower than that obtained after the prior dose; and f) identifying an optimal dose of the therapeutic agent for treating the disease, wherein the optimal dose is a dose that causes an optimal decrease of the level or rate of binding or internalization of the binding moiety. In one embodiment, if in step e) the level or rate of binding or internalization of said binding moiety obtained after the follow-up dose is higher than that obtained after the prior dose, the subsequent dose is reduced such that the reduced dose is a dose that causes an optimal decrease of said level or rate of binding or internalization. In one embodiment, the reduced dose is the prior dose.

In another embodiment, there is provided a targeting molecule that binds to LRRC15, the targeting molecule comprises the amino acid sequences of SEQ ID NO:1 and SEQ ID NO:2. In another embodiment, there is provided a conjugate comprising this LRRC15 targeting molecule.

These and other aspects of the invention will be appreciated from the ensuing descriptions of the figures and detailed description of the invention.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 2B shows percent cellular DUNP19 internalization over time which was retrieved by quantifying plasma membrane localization (DUNP19 incubation at 4° C.) relative to cytosolic signal (defined by DAPI and LAMP1).

FIG. 3A shows that U118 tumors had the highest LRRC15-radiotracer accumulation compared to other organs at all studied time-points (left-to-right for each organ and tumor: 24, 48, 72 hrs). FIG. 3B shows targeting specificity of DUNP19, wherein the first column shows tumor uptake of a Lutetium-177 labeled non-specific huIgG1 in LRRC15 expressing xenografts (U118), the second column shows [$^{177}$Lu]DUNP19 uptake in a non-LRRC15 expressing tumor model (LNCaP), and the third column shows [$^{177}$Lu]DUNP19 uptake in LRRC15-expressing U118 cells.

FIGS. 4A and 4C shows [$^{177}$Lu]DUNP19 evaluated in LRRC15$^+$ (SAOS2 and U118) and LRRC15$^-$ (LN-CaP) s.c. xenografts at multiple time-points (n=4 per group) after i.v. injection. [$^{177}$Lu]DUNP19 showed high tumor uptake with low accumulation in healthy organs and rapid elimination. [$^{177}$Lu]DUNP19 tumor uptake correlated with target expression; uptake in SAOS2 s.c. tumors were higher than in U118 at all studied time-points (left-to-right for each organ and SAOS2: 6, 24, 48, 72, 168 and 336 hrs; left-to-right for U118: 24, 48 and 72 hrs). FIG. 4B shows targeting of LRRC15 was specific; accumulated levels of [$^{177}$Lu] DUNP19 in LRRC15$^+$ U118 and SAOS2 tumors at 48 hours post-injection were significantly higher (P<0.001) than in i) LRRC15$^-$ lesions (LNCaP), and ii) the EPR effects in U118 tumors, i.e. uptake of a radiolabeled non-specific radioimmuno-conjugate ([$^{177}$Lu]IgG$_1$). FIG. 4D shows anti-tumor effects of LRRC15-targeted RIT; a single dose (10 MBq) i.v. injected [$^{177}$Lu]DUNP19 significantly (P<0.001) reduced tumor (SAOS2) volume compared to non-treated (n=10/group).

FIG. 5A shows accumulation of i.v. administered [$^{64}$Cu]DUNP19 in LRRC15$^+$ SAOS2 s.c. xenograft. Shown is a direct comparison of [$^{18}$F]NaF PET bone scan and [$^{64}$Cu]DUNP19 LRRC15 PET. FIG. 5B is a series of PET images displaying robust tumor specific accumulation over time. FIG. 5C shows quantified tumor and blood specific activity in SAOS2 s.c. tumor model after i.v. injection of [$^{64}$Cu]DUNP19.

DETAILED DESCRIPTION OF THE INVENTION

Figure 1:
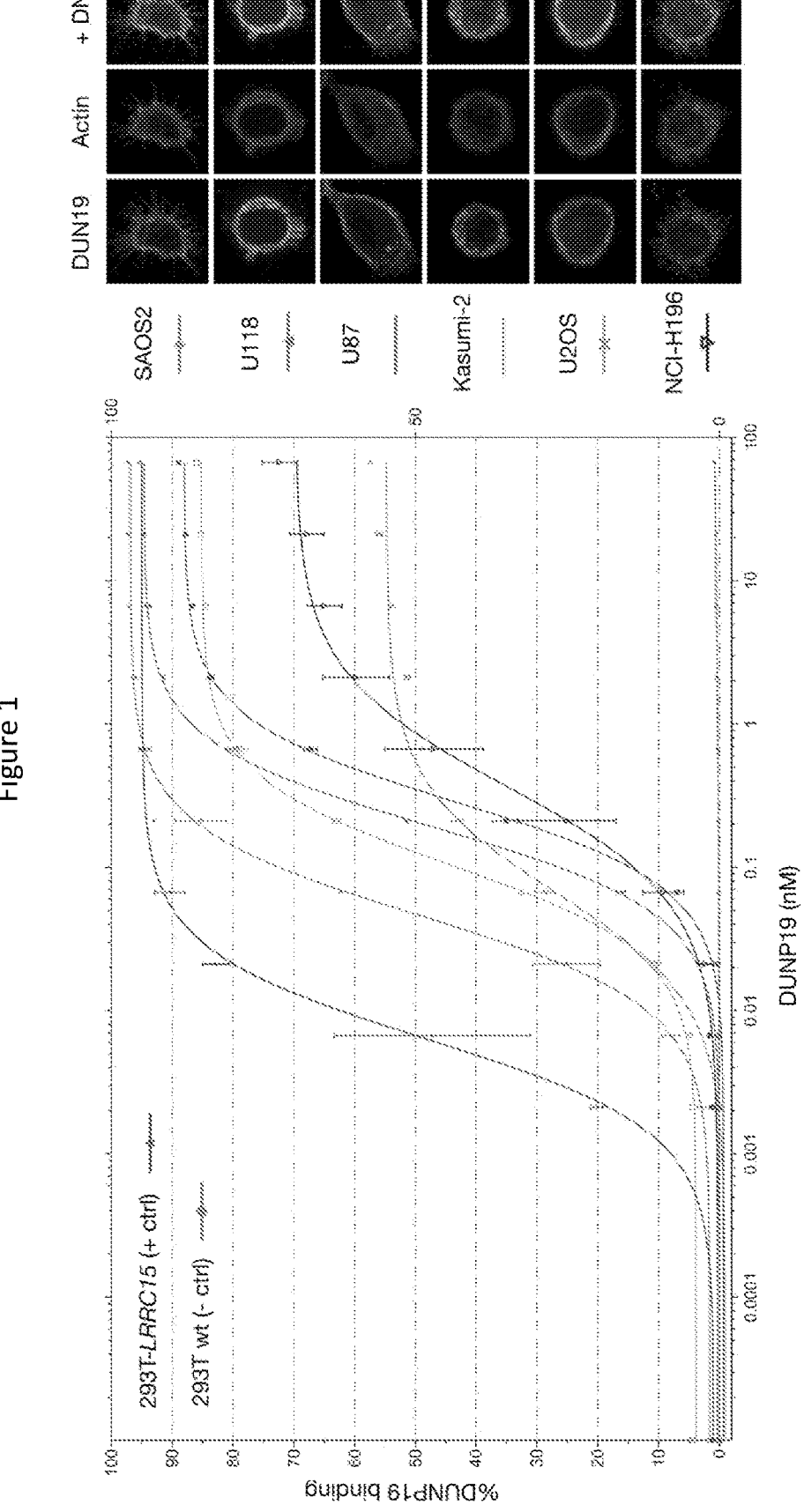
FIG. 1 shows cellular binding specificity of anti-LRRC15 mAb DUNP19. Binding specificity of DUNP19 was studied by flow cytometry using a range of cell lines derived from different tumor types with diverse LRRC15 expression levels (left panel). Confocal microscopy was utilized to further study cellular binding of DUNP19 (right panel). First column shows staining with DUNP19, the second column shows cells co-stained with actin, and the third column shows merged images showing co-staining with DNA using phalloidin and DAPI stains.

The tumor stroma plays a critical role in tumor initiation, progression and resistance to therapeutic compounds as well as inherent immunological defense mechanisms. Leucine-rich repeat-containing protein 15 (LRRC15) is a TGF-beta governed protein that is expressed by cancer-associated fibroblasts (CAFs) and by a subset of cancer cells of mesenchymal origin. Importantly, expression is coupled to poor response to checkpoint blockade in several tumor types. The present disclosure presents radiotheranostic applications based on a recently developed monoclonal anti-LRRC15 antibody (mAb DUNP19) that is specifically internalized by cells expressing LRRC15. It is expected that LRRC15-targeted radiotheranostics (such as DUNP19 antibody) could significantly improve diagnosis and enable treatment of a broad range of malignancies.

The present disclosure addresses a fundamental unmet need in clinical management of several late-stage and disseminated cancers by employing a unique strategy targeting LRRC15, a TGF-β governed biomarker specifically over-expressed in mesenchymal stem cell-derived cancer cells and tumor stroma. Preclinical results obtained in vitro and in rodent models demonstrate intracellular delivery of this LRRC15-directed platform. In one embodiment, the present disclosure presents key experiments to define diagnostic and therapeutic utilities of [$^{89}$Zr]DUNP19, [$^{225}$Ac]DUNP19 and [$^{177}$Lu]DUNP19. Factors that govern the magnitude and distribution of the α- and β-particle emitting constructs can be evaluated. Moreover, the efficacy of targeting LRRC15 for monitoring TGF-β activity and compounds inhibiting the TGF-β receptor can also be tested. These studies will significantly advance radio-theranostic approaches toward clinical application for sustained treatment and monitoring of several late stage malignant diseases.

Disclosed herein is a highly innovative and unique non-invasive immuno-theranostic platform applicable for molecularly specific imaging of therapy resistant tumors containing immunoregulatory cancer cells driven by TGF-β as well as treatment of a wide range of primary, late-stage and disseminated malignancies. In one embodiment, the central component of the technology is a highly specific mAb (DUNP19) targeting LRRC15, which is applicable for targeting TGF-β driven CAFs within the tumor stroma of many cancer indications, as well as direct targeting of cancer cells of mesenchymal tumors (e.g., sarcomas, glioblastoma multiforme). While the potential of stromal targeting is widely recognized, innovative approaches have been difficult to implement, largely because of a scarcity of optimal targets with high tumor specificity. Unlike other CAF proteins, LRRC15 expression is very low in non-cancerous tissues and absent in lymph node stroma and normal pancreas. The cancer specific expression profile, correlation to immunotherapy resistance and inducibility by TGF-β differentiate LRRC15 from other commonly used mesenchymal markers.

DUNP19 has several advantages over other anti-LRRC15 antibodies. In addition to having significantly higher affinity, DUNP19 binds to a developmentally advantageous and phylogenetically conserved epitope. This feature enables evaluations in wild-type (wt) animal models, avoiding the need to genetically engineer human LRRC15 expression into the host genome. Importantly, DUNP19 is rapidly and effectively internalized by target cells, which is critical for targeted radiopharmaceuticals emitting short-range particles (e.g., high-LET alpha or Auger emitters). The internalization also renders other possibilities such as exploiting DUNP19 for targeting intracellular proteins with molecules that do not naturally cross the cell membrane.

Thus, LRRC15 is an optimal targetable biomarker that can be leveraged for both non-invasive imaging and therapy, in particular by a binding moiety such as an antibody that is internalized by LRRC15-expressing cells. The present disclosure developed and optimized a mAb, DUNP19, which demonstrates specific targeting and effective internalization by LRRC15-expressing cells. Other LRRC15-targeted antibodies that are internalized by LRRC15-expressing cells are also embraced herein. In one embodiment, DUNP19 can be applied for the following clinical applications:

I. Labeled with one or more therapeutic radionuclides: e.g., elimination of tumor cells that express LRRC15, and/or eliciting anti-tumor response by inflicting irreversible damage to the tumor or tumor stroma, thereby disrupting tumor stroma's ability to facilitate and maintain the tumor microenvironment, paracrine support, drug resistance and inhibition of immune system. Targeting to LRRC15-expressing, disease-associated tissues other than tumors is another application useful, for example, in autoimmune diseases such as but not limited to rheumatoid arthritis.

II. Labeled with positron emitting radionuclides: e.g., non-invasive diagnostic imaging of very aggressive pathological features and immunotherapy-resistant disease by non-invasive detection and quantification of TGF-β governed LRRC15+ CAFs, and/or assisting clinical decision-making, such as monitoring response and dose adjustment of drugs that directly or distally modulate TGF-β signaling.

In one embodiment, it is expected that pharmacological strategies aimed at eliminating tumor-associated stroma or impeding immune-suppressive pathways will have impactful anti-tumor effects either as monotherapies, or in combination with compounds directing the innate immune system. Non-invasive imaging of LRRC15 and quantification of uptake has great potential for localization of aggressive tumors as well as detection and quantification of molecular features correlating to immunotherapy resistance. It is further hypothesized that LRRC15-PET would be applicable for monitoring down-stream activity of TGF-beta receptor blockers, which are currently hampered by a narrow dose-range and effects exclusive to certain tumor cell origins.

In one embodiment, it is anticipated that the anti-neoplastic effects of anti-LRRC15 radioimmunotherapy (RIT) would be contingent on the applied linear energy transfer (LET) and the cellular localization of target expression. In brief, it is believed that intracellular dose deposition of short-range high-LET in LRRC15-expressing CAFs will result in specific eradication of the tumor stoma, causing anti-neoplastic effects through acute microenvironmental changes, exhaustion of paracrine support, improved drug infiltration and increased susceptibility to immunotherapies and components of the intrinsic immune system. Although utilization of low-LET LRRC15-radioimmunotherapy (RIT) may result in less effective obliteration of the targeted CAFs, crossfire effects from the long track path-length will translate into damage of the near-by tumor cells.

Methods of Use

In one embodiment, there is provided a method of using the binding moiety targeting LRRC15 disclosed herein to treat a disease having disease-associated tissue that is derived from or associated with mesenchymal stem cells. In another embodiment, the binding moiety targeting LRRC15 disclosed herein is provided for a use in treating a disease having disease-associated tissue that is derived from or associated with mesenchymal stem cells. The method or use comprises the step of administering to a patient a binding moiety targeting LRRC15 expressed on cells in the disease-associated tissue, wherein the binding moiety is associated with a cytotoxic agent and the binding moiety is internalized by cells in the disease-associated tissue, thereby delivering the cytotoxic agent to the disease-associated tissue. In one embodiment, the disease is an autoimmune disease (e.g., rheumatoid arthritis). In another embodiment, the disease-associated tissue comprises tumor or tumor stromal cells. Representative examples of tumors include, but are not limited to, pancreatic tumor, ovarian carcinoma, glioblastoma multiforme, osteosarcoma, breast tumor, head and neck tumor, lung tumor, bladder tumor, colorectal tumor, hepatocellular tumor, testicular tumor, endometrial tumor, gastric tumor, renal tumor, prostate tumor, sarcoma, or melanoma. The prostate cancer can be androgen receptor negative or androgen independent. In another embodiment, the tumor is metastatic. In another embodiment, the tumor stromal cells comprise fibroblasts, mesenchymal cells, epithelial cells, or any combination thereof.

In one embodiment, the binding moiety can be a single-chain variable fragment (scFv), a Fv fragment, an antigen binding fragment (Fab), a F(ab')2 fragment, a bispecific T cell engager, or a chimeric antigen receptor (CAR). In one embodiment, the binding moiety has picomolar affinity for LRRC15. In one embodiment, the binding moiety is an antibody. In one embodiment, the antibody binds to a phylogenetically conserved epitope on LRRC15 (e.g. to an epitope on mammalian LRRC15). In one embodiment, the antibody is a humanized monoclonal antibody, for example, a monoclonal antibody comprising a variable heavy chain having the sequence of SEQ ID NO:1 and a variable light chain having the sequence of SEQ ID NO:2. In another embodiment, the monoclonal antibody is an afucosylated antibody or a low-fucose variant thereof.

In one embodiment, the cytotoxic agent associated with the binding moiety is a therapeutic radionuclide. The therapeutic radionuclide can be an alpha particle emitter, a beta particle emitter, an Auger electron emitter, a gamma-ray emitter or a combination thereof. Examples of alpha particle emitters include, but are not limited to, uranium, radium, thorium, and actinium. Examples of beta particle emitters include, but are not limited to, uranium, thorium, actinium, bismuth, thallium, strontium, caesium, lutetium, and zirconium. Examples of Auger electron emitters include, but are not limited to, technetium, indium, and iodine. Examples of gamma-ray emitters include, but are not limited to, uranium, thorium, actinium, cobalt, caesium, and technetium. In another embodiment, the cytotoxic agent is monomethyl auristatin E, mertansine, maytansanoid, a taxane, streptonigrin, geldanamycin, camptothecin, calicheamicin, duocarmycin, or a derivative or analogue thereof. In one embodiment, the cytotoxic agent is covalently bound to the binding moiety. In one embodiment the cytotoxic agent is non-covalently bound to the binding moiety. In one embodiment the binding moiety is radiolabeled with the cytotoxic agent. In one embodiment cytotoxic agent is conjugated to the antibody by a chelating agent. In some embodiments the conjugation is direct, i.e., the cytotoxic agent is directly conjugated to the binding moiety. In some embodiments, the conjugation is indirect, i.e., the binding moiety and the cytotoxic agent are conjugated in vivo, also known as a pretargeting method. Such conjugation methods are known in the art, for example in the making of antibody drug conjugates (ADC), and will be readily prepared for the particular agent being conjugated.

In another embodiment, there is provided a method of using the binding moiety targeting LRRC15 disclosed herein to image disease-associated tissue that is derived from or associated with mesenchymal stem cells. In another embodiment, the binding moiety targeting LRRC15 disclosed herein is provided for a use in imaging disease-associated tissue that is derived from or associated with mesenchymal stem cells. The method or use comprises the step of administering to a patient a binding moiety targeting LRRC15 expressed on cells in the disease-associated tissue, wherein the binding moiety is associated with an imaging agent and the binding moiety is internalized by cells in the disease-associated tissue, thereby delivering the imaging agent to the disease-associated tissue. In one embodiment, the disease is an autoimmune disease (e.g., rheumatoid arthritis). In another embodiment, the disease-associated tissue comprises tumor or tumor stromal cells. Examples of tumors and tumor stromal cells have been listed above.

In one embodiment, the binding moiety used in the above imaging method can be a single-chain variable fragment (scFv), a Fv fragment, an antigen binding fragment (Fab), or a F(ab')2 fragment. In one embodiment, the binding moiety has picomolar affinity for LRRC15. In one embodiment, the binding moiety is an antibody. In one embodiment, the antibody binds to a phylogenetically conserved epitope on LRRC15 (e.g., to an epitope on mammalian LRRC15). In one embodiment, the antibody is a humanized monoclonal antibody, for example, a monoclonal antibody comprising a variable heavy chain having the sequence of SEQ ID NO:1 and a variable light chain having the sequence of SEQ ID NO:2. In another embodiment, the monoclonal antibody is an afucosylated antibody or a low-fucose variant thereof. In one embodiment, the imaging agent is a positron emitter. Examples of positron emitters include, but are not limited to, $^{18}$F, $^{15}$O, $^{11}$C, $^{13}$N, $^{82}$Rb, $^{68}$Ga, $^{64}$Cu, $^{76}$Br, $^{86}$Y, $^{89}$Zr, and $^{124}$I. In one embodiment the imaging agent is non-covalently bound to the binding moiety. In one embodiment the binding moiety is radiolabeled with the imaging agent. In one embodiment the imaging agent is conjugated to the antibody by a chelating agent. In some embodiments the conjugation is direct, i.e., the imaging agent is directly conjugated to the binding moiety. In some embodiments, the conjugation is indirect, i.e., the binding moiety and the imaging agent are conjugated in vivo, also known as a pretargeting method. Such conjugation methods are known in the art and will be readily prepared for the particular agent being conjugated.

In order to identify the exact anatomical location of uptake of a binding moiety of the invention such as DUNP19, the acquired PET images will be combined with and co-registered with anatomical images obtained using a CT or MRI. In one embodiment, PET/CT imaging of the patients/subjects will be performed with a Siemens Bio-graph64 mCT PET/CT system, or similar system. PET images will be acquired at several time-points after intravenous administration of binding moiety conjugated to an imaging agent, such as DUNP19 labeled with a positron emitting radionuclide (such as Zirconium-89 or Yttrium-86). As the radioisotope on the antibody undergoes positron emission decay, it emits a positron, an antiparticle of the electron with opposite charge. The emitted positron travels in tissue for a short distance (typically less than 1 mm, but dependent on the isotope), during which time it loses kinetic energy, until it decelerates to a point where it can interact with an electron. The encounter annihilates both electron and positron, producing a pair of annihilation (gamma) photons moving in approximately opposite directions. These are detected when they reach a scintillator in the PET scanning device, creating a burst of light, which is detected by photomultiplier tubes or silicon avalanche photodiodes. A PET examination of a patient/subject will consist of a combination of a series of image acquisitions obtained at several bed positions covering the whole body or region/area of interest. The estimated scan time per bed position is approximately 15 min, but can (as a result of decay) vary depending on interest of a specific region, injected amount of activity or time after injection. The total imaging time (including gaps between scans) can be estimated to approximately an hour. Data will be exported in raw format and the rigid body (3 degrees of freedom) co-registration between PET and CT data will be performed in Amira 5.3.3 (FEI), or similar computer software. Siemens Syngo MultiModality Workplace software (version VE40A), or similar, will be used to analyze and quantify uptake on PET images. Other methods for PET scanning and image analysis are fully embraced herein.

In another embodiment, the binding moiety targeting LRRC15 associated with an imaging or cytotoxic agent may be used for imaging or for therapy in various acute and chronic lung diseases such as those cause by viral infections, including but not limited to Covid-19 and other infectious agents. In one embodiment, in acute lung diseases, as well as in chronic diseases, such as but not limited to chronic obstructive lung disease (COLD), chronic obstructive airway disease (COAD), chronic bronchitis, emphysema and pulmonary emphysema, TGF-β activity is increased, which activates mesenchymal stem cell differentiation into epithelial stem cells before reestablishing various epithelial cells resulting in fibrosis. During acute or chronic lung injury, an inappropriate immune response and/or aberrant repair process causes irreversible damage in lung tissue and often results in the development of fibrosis followed by decline in lung function. Moreover, some viral infections decrease the hosts' ability to recruit a proper and effective immune response by directly increasing TGF-β, which also is a potent inhibitor of the IL-2 signaling pathway and is involved in MSC-mediated G1 cell cycle arrest of activated T cells, which will decrease the hosts' ability to recruit a proper and effective immune response.

Thus, in one embodiment, inhibiting TGF-beta activity can stop such processes, and applying LRRC15 imaging as described herein as a read-out of TGF-β activity will have implications for understanding and regulating dosing of TGF-beta inhibitors.

In one embodiment, a method is provided for imaging lung tissue and lung injury in a patient by following the guidance described herein. In one embodiment, the course of the disease may be monitored following the guidance described herein. In one embodiment, the methods described herein may be used to select patients with lung injury for treatment. In one embodiment the methods described herein may be used to titrate the dose of a TGF-β inhibitor or other therapeutic agent for treatment of lung injury. In one embodiment, the therapeutic use of TGF-β inhibitor therapy is known to be complex and dose selection and titration of the optimal dose important in optimizing therapeutic effectiveness and not eliciting unwanted effects from exacerbating inflammation or off-target toxicity. The methods described herein for dose determination and adjustment are useful for the selection, monitoring, and titration of treatment of lung diseases including the inflammatory response, described herein in acute and chronic lung diseases.

In one embodiment, a method for treating a lung injury in a patient is provided by administering to the patient a binding moiety targeting LRRC15 wherein the binding moiety is associated with a cytotoxic agent and the binding moiety is internalized by cells in the lungs.

In any of the foregoing embodiments, the LRRC15 binding moiety may comprise variable heavy chain having the sequence of SEQ ID NO:1 and a variable light chain having the sequence of SEQ ID NO:2. In one embodiment, the binding moiety is DUNP19. In any of the foregoing embodiments, a LRRC15 binding moiety may comprise the complementarity determining regions of the aforementioned sequences, or of an antibody to LRRC15 that is internalized by its target cells.

In any of the embodiments herein, the LRRC15 binding moiety may be a bispecific or trispecific antibody, engineered with at least one binding specificity to LRRC15. Such antibodies may be used for any of the purposes herein described. In another embodiment, a bi- or trispecific antibody may have at least one binding specificity for LRRC15, and at least one binding specificity for another ligand. In one embodiment, the other ligand is TFG-β. In one embodiment, a bispecific or trispecific antibody that binds LRRC15 and TFG-β may be used to reduce TGF-β levels or inhibit activity at the site of cells or tissues expressing LRRC15. In one embodiment, because TGF-β receptor activity governs LRRC15 expression, use of the bi- or trispecific antibody will decrease the effect of the TGF-β. In one embodiment, decreasing the effect of TGF-β will reduce the expression of LRRC15. In one embodiment, such modality is generated by incorporating the LRRC15 specific-binding site of DUNP19 as one, or two, of a bi-specific or tri-specific antibody's binding site/sites, combined with two, or one, binding sites specific for TGF-β. Examples of anti-TGF-β antibodies include, but are not limited to, fresolimumab. In one embodiment, fresolimumab comprises a variable heavy chain having the sequence of SEQ ID NO:3 and a variable light chain having the sequence of SEQ ID NO:4.

In another embodiment, there is provided a method of using the binding moiety targeting LRRC15 disclosed herein to select a patient for therapy with a molecule that inhibits TGF-β receptor signaling, wherein the patient has or is suspected of having a disease comprising disease-associated tissue that is derived from or associated with mesenchymal stem cells. In another embodiment, the binding moiety targeting LRRC15 disclosed herein is provided for a use in selecting a patient for therapy with a molecule that inhibits TGF-β receptor signaling, wherein the patient has or is suspected of having a disease comprising disease-associated tissue that is derived from or associated with mesenchymal stem cells. The method or use comprises the steps of: a) administering to the patient a binding moiety targeting LRRC15 expressed on cells in the disease-associated tissue, wherein the binding moiety is associated with an imaging agent and the binding moiety is internalized by cells in said disease-associated tissue; b) determining a level of binding or internalization of the binding moiety; and c) when a patient is found to exhibit a higher level of binding or internalization of the binding moiety as compared to a control level in a control subject, the patient is selected for and treated with the therapy. In one embodiment, the control subject is a healthy subject or one without the disease in question. Examples of disease, tumors or tumor stromal cells have been listed above. Examples of the imaging agent and the binding moiety have been discussed above. In one embodiment, the binding moiety comprises a variable heavy chain having the sequence of SEQ ID NO:1 and a variable light chain having the sequence of SEQ ID NO:2.

In another embodiment, there is provided a method of using the binding moiety targeting LRRC15 disclosed herein to determine a dose of a therapeutic agent for treating a disease in a patient, wherein the disease comprises disease-associated tissue that is derived from or associated with mesenchymal stem cells. In another embodiment, the binding moiety targeting LRRC15 disclosed herein is provided for a use in determining a dose of a therapeutic agent for treating a disease in a patient, wherein the disease comprises disease-associated tissue that is derived from or associated with mesenchymal stem cells. The method or use comprises the steps of: a) administering to the patient a first dose or a prior dose of the therapeutic agent; b) administering to the patient a binding moiety targeting LRRC15 expressed on cells in the disease-associated tissue, the binding moiety is associated with an imaging agent and the binding moiety is internalized by cells in the disease-associated tissue; c) determining a level or rate of binding or internalization of the binding moiety; d) administering to the patient a follow-up dose of the therapeutic agent, the follow-up dose is higher than the first or prior dose, and repeating steps b) and c); e) repeating step d) when the level or rate of binding or internalization of the binding moiety obtained after the follow-up dose is lower than that obtained after the prior dose; and f) identifying an optimal dose of the therapeutic agent for treating the disease, wherein the optimal dose is a dose that causes an optimal decrease of the level or rate of binding or internalization of the binding moiety.

In one embodiment, if in foregoing method or use the level or rate of binding or internalization of said binding moiety obtained after the follow-up dose is higher than that obtained after the prior dose, the subsequent dose is reduced such that the reduced dose is a dose that causes an optimal decrease of said level or rate of binding or internalization. In one embodiment, the reduced dose is the prior dose.

In one embodiment, the therapeutic agent in the foregoing method or use is a molecule that inhibits TGF-β receptor signaling, such as but not limited to small molecule inhibitors of the TGF-β receptor I such as galunisertib. Examples of disease, tumors or tumor stromal cells have been listed above. Examples of the imaging agent and the binding moiety have been discussed above. In one embodiment, the binding moiety comprises a variable heavy chain having the sequence of SEQ ID NO:1 and a variable light chain having the sequence of SEQ ID NO:2.

The principle of the above method of dosage determination is that a patient is put on an incremental dosing schedule, and an effective dose level can be found after several doses. Doses exceeding the effective or optimal dose are expected to lead to adverse effects, e.g., increases in LRRC15 expression and/or tumor growth and/or toxicity. In one embodiment, after each dose is administered, the LRRC15 level is determined by imaging as disclosed herein to evaluate reduced LRRC15 expression (which is an indication of efficacy). The cycle of dosing and imaging continues as the dosage is increased. Once a dose level leads to adverse effects, e.g., an increase in LRRC15 expression or toxicity, a lower dose such as the dosage prior to such adverse effects is identified as the effective or optimal dose.

In another embodiment, there is provided a targeting molecule that binds to LRRC15, the targeting molecule comprises the amino acid sequences of SEQ ID NO:1 and SEQ ID NO:2. In one embodiment, the targeting molecule comprises one or more polypeptides. In one embodiment, the targeting molecule is an antibody, a Fv fragment, an antigen binding fragment (Fab), a F(ab')2 fragment, a single chain variable fragment (scFv), a bispecific T cell engager, or a chimeric antigen receptor (CAR). In one embodiment, the antibody is a humanized monoclonal antibody. In one embodiment, the monoclonal antibody is an afucosylated antibody or a low-fucose variant thereof.

In another embodiment, the targeting molecule that binds to LRRC15 can be a bispecific or trispecific antibody, engineered with at least one binding specificity to LRRC15. Such antibodies may be used for any of the purposes herein described. In one embodiment, a bi- or trispecific antibody may have at least one binding specificity for LRRC15, and at least one binding specificity for another ligand. In one embodiment, the other ligand is TFG-β. In one embodiment, a bispecific or trispecific antibody that binds LRRC15 and TFG-β may be used to reduce TGF-β levels or inhibit activity at the site of cells or tissues expressing LRRC15. In one embodiment, because TGF-β receptor activity governs LRRC15 expression, use of the bi- or trispecific antibody will decrease the effect of the TGF-β. In one embodiment, decreasing the effect of TGF-β will reduce the expression of LRRC15. In one embodiment, such modality is generated by incorporating the LRRC15 specific-binding site of DUNP19 as one, or two, of a bi-specific or tri-specific antibody's binding site/sites, combined with two, or one, binding sites specific for TGF-β. Examples of anti-TGF-β antibodies include, but are not limited to, fresolimumab. In one embodiment, fresolimumab comprises a variable heavy chain having the sequence of SEQ ID NO:3 and a variable light chain having the sequence of SEQ ID NO:4. Methods for the preparation of bispecific and trispecific antibodies may be found in, for example, Labrijn et al., Bispecific antibodies: a mechanistic review of the pipeline, Nature Review Drug Discovery 18:585-608 (2019); Brinkmann et al., The making of bispecific antibodies, MAbs. February/ March 2017; 9(2):182-212; Sedykh et al., Bispecific antibodies: design, therapy, perspectives. Drug Des Devel Ther. 2018 Jan. 22; 12:195-208; Wu et al., Building blocks for bispecific and trispecific antibodies. Methods. 2019 Feb. 1; 154:3-9; and Runcie et al., Bi-specific and tri-specific antibodies—the next big thing in solid tumor therapeutics, Mol Med, 2018; 24:50, the contents of which are incorporated herein by reference.

In another embodiment, there is provided a conjugate comprising the LRRC15 targeting molecule disclosed herein. In one embodiment, the conjugate comprises the LRRC15 targeting molecule disclosed herein and a cyto- toxic or imaging agent. The cytotoxic or imaging agent can be a therapeutic radionuclide or a positron emitter. Examples of therapeutic radionuclide and positron emitter have been shown above. In one embodiment, the cytotoxic or imaging agent is covalently bound to the binding moiety. In one embodiment the cytotoxic or imaging agent is non-cova- lently bound to the binding moiety. In one embodiment the binding moiety is radiolabeled with the cytotoxic or imaging agent. In one embodiment cytotoxic or imaging agent is conjugated to the antibody by a chelating agent. In some embodiments the conjugation is direct, i.e., the cytotoxic or imaging agent is directly conjugated to the binding moiety.

In some embodiments, the conjugation is indirect, i.e., the binding moiety and the cytotoxic or imaging agent are conjugated in vivo, also known as a pretargeting method.

Cytotoxic agent refers to any therapeutically useful com- ponent that is associated, covalently or on-covalently, with an antibody or LRRC15 binding moiety of the invention. In addition to the cytotoxic agents described here, such other agents include, but are not limited to, antibodies, antibody fragments, antigen-binding moieties, nucleic acids, oligo- nucleotides, cytokines, growth factors, chemokines, enzymes, therapeutic proteins, fluorophores and steroids. In one embodiment the cytotoxic agent is a TGF-β inhibitor or a TGF-β receptor inhibitor. In some embodiments, the cytotoxic agent is a agent that is toxic to cells, such as cancer cells. In some embodiments, the cytotoxic agent is an agent that is toxic to cells derived from or associated with mes- enchymal stem cells or mesenchymal cells.

As used herein, the terms "comprise", "comprises", "comprising", "includes", "including", "having" and their conjugates mean "including but not limited to".

As used herein, the singular form "a", "an" and "the" include plural references unless the context clearly dictates otherwise. For example, the term "an enzyme" or "at least one enzyme" may include a plurality of enzymes, including mixtures thereof.

Throughout this application, various embodiments of the present disclosure may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed sub- ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchange- ably and are meant to include the first and second indicated numbers and all the fractional and integral numerals ther- ebetween.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exem- plary methods and/or materials are described below. In case of conflict, the patent specification, including definitions, will control. In addition, the materials, methods, and examples are illustrative only and are not intended to be necessarily limiting. Each literature reference or other cita- tion referred to herein is incorporated herein by reference in its entirety.

In the description presented herein, each of the steps of the invention and variations thereof are described. This description is not intended to be limiting and changes in the components, sequence of steps, and other variations would be understood to be within the scope of the present inven- tion.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples. While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLE 1

Anti-LRRC15 Antibody, DUNP19

Figures 2A, 2B, 2C:
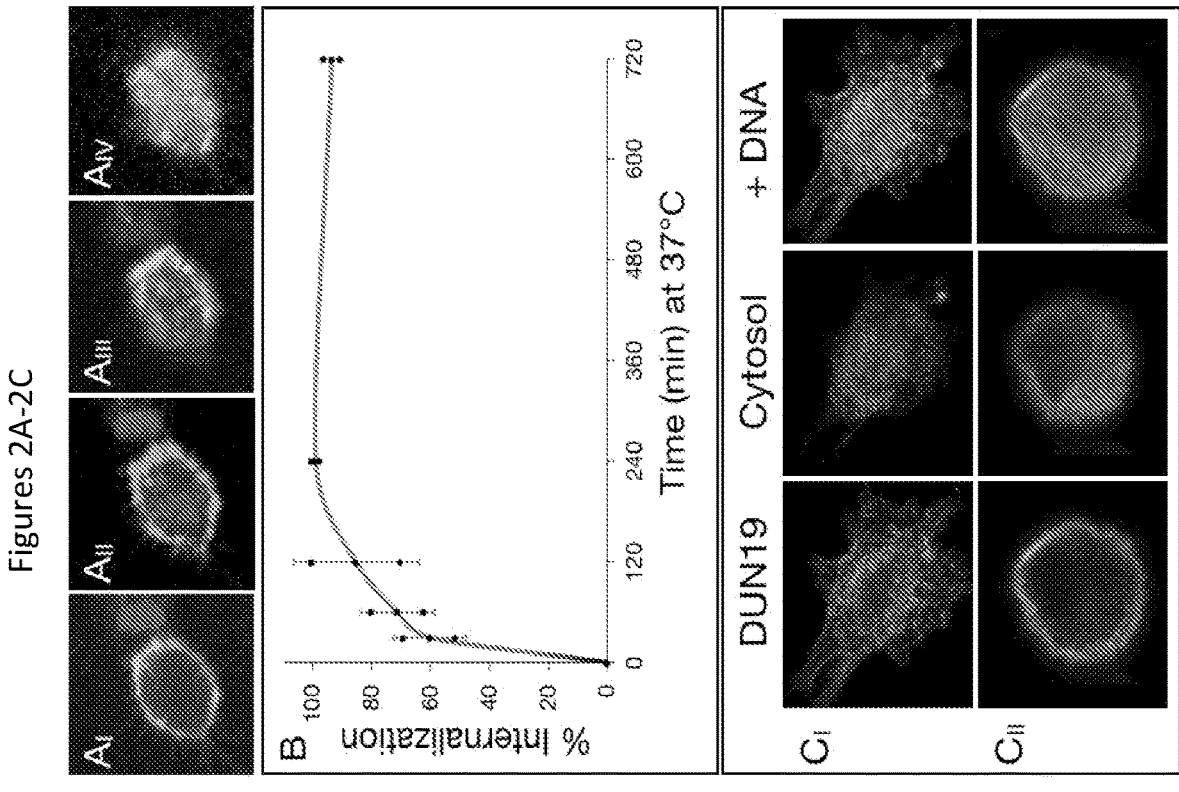
FIGS. 2A-2C show cellular internalization of LRRC15 mAb DUNP19 at 37° C. The panels are confocal images of SAOS2 cells incubated at 4° C. with Alexa-488 labeled DUNP19 (Fig. AI), or incubated at 37° C. with Alexa-488 labeled DUNP19 for 30 (Fig. AII), 60 (Fig. AIII), 120 (Fig. AIV), or 240 minutes (Fig. CI). Fig. CII shows staining at 4° C.

DUNP19 was developed by humanization of a hybridoma mAb generated from immunizing mice with stably transfected LRRC15-expressing 3T3 cells. Results obtained by flow-cytometry demonstrate that DUNP19 has high in vitro binding specificity to a range of cells with wild-type (wt) and transfected LRRC15 expression, while no binding was observed to negative cells (FIG. 1). Liquid chromatography-mass spectrometry (LC-MS) analysis of DUNP19 incubated with LRRC15-expressing cell lines confirmed molecular binding specificity. It is further found that DUNP19 binds to a phylogenetically conserved epitope. DUNP19 binds specifically to 293T cells transfected with rodent or non-human primate LRRC15. LigandTracer (Ridgeview Instruments) was utilized to assess binding interaction between live cells and Lutetium-177 labeled DUNP19 ($[^{177}Lu]$DUNP19). These analyses showed that $[^{177}Lu]$DUNP19 binds target cells with picomolar affinity (3.29E-10 m). Furthermore, confocal imaging revealed that DUNP19 is rapidly internalized by LRRC15-expressing cells (FIG. 2A-C). Internalization rate was studied by quantifying emitted fluorescence over time from SAOS2 cells incubated with pH-responsive dye-labeled DUNP19. Identification of colocalization of Alexa-488 labeled DUNP19 with intracellular markers (DAPI and LAMP1) in SAOS2 cells over time was applied to further confirm time of internalization. These studies demonstrated that >50% and 100% of DUNP19 was internalized at 30 minutes and 3 hours, respectively.

Figures 3A, 3B:
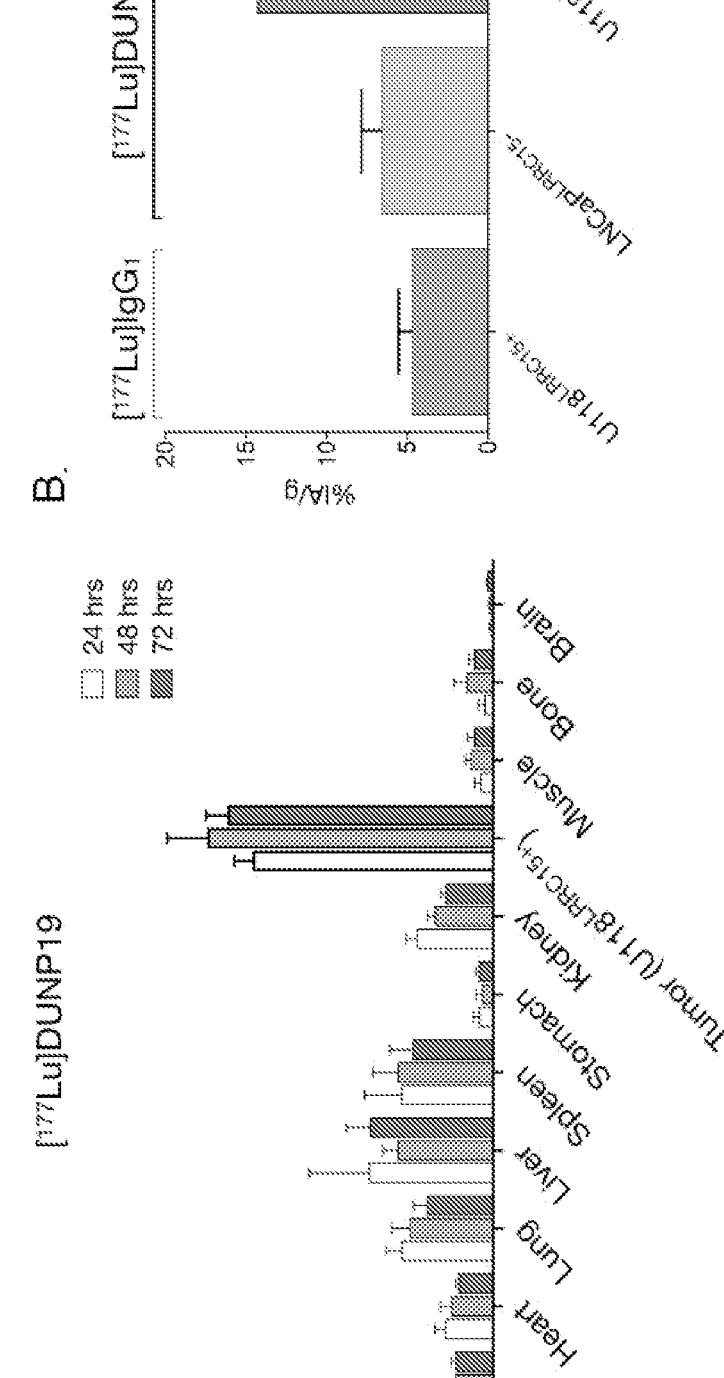
FIGS. 3A-3B show in vivo biodistribution of [$^{177}$Lu] DUNP19. Targeting and accumulation of i.v. administered [$^{177}$Lu]DUNP19 was evaluated in LRRC15-expressing U118 xenografts.

In vivo targeting specificity was evaluated by studying tissue biodistribution of systemically (i.v.) injected $[^{177}Lu]$ DUNP19 in subcutaneous (s.c.) tumor models. Radio-conjugate uptake, expressed as percent injected activity per gram (% IA/g), was assessed in 12 different tissues and blood at 24, 48 and 72 hours after injection. U118 tumors were found to have the highest % IA/g of $[^{177}Lu]$DUNP19 at all timepoints (FIG. 3A). Further, uptakes of $[^{177}Lu]$ DUNP19 and a non-specific Lutetium-177 labeled mAb were negligible in LRRC15 negative (LNCaP) and U118 tumors, respectively (FIG. 3B).

In one embodiment, the variable heavy chain of DUNP19 comprises the following sequence:

```
                                          (SEQ ID NO: 1)
QVQLVQSGAEVKKPGASVKVSCKASGYTFTDYYIHWVRQAPGQGLEWMGW

INPNSDGTNYAQNFLGRVTMTRDTSISTAYMELSRLRSDDSAVYHCVREG

RYSTSPFDYWGQGTLVTVSS.
```

In one embodiment, the variable light chain of DUNP19 comprises the following sequence:

```
                                          (SEQ ID NO: 2)
DIVMTQSPDSLAVSLGERATINCKSSQSVLYSSNNRNYLAWYQQKPGQPP

KLFIYWSSTRESGVPDRFSGSGSGTDFTLTISSLQAEDVAVYYCQQYYST

PFTFGQGTKLEIKR.
```

EXAMPLE 2

In Vivo Binding Specificity and Biodistribution Profile of DUNP19

One object of the present example is to further evaluate LRRC15-targeted radioimmunotheranostics in a range of immuno-competent and immuno-suppressed tumor models with different LRRC15 expression profiles. In one embodiment, tumor uptake and tissue kinetics of the following DUNP19 antibodies would be examined: i) DUNP19 labeled with Zirconium-89 ($^{89}Zr$-DFO-DUNP19, $[^{89}Zr]$ DUNP), which is a positron emitting radiometal with an optimal half-life (3.3 days) for immuno-PET imaging; ii) DUNP19 labeled with beta-emitter Lutetium-177 ($^{177}Lu$-DOTA-DUNP19, $[^{177}Lu]$DUNP) (half-life of 6.7 days), and iii) DUNP19 labeled with Actinium-225 ($^{225}Ac$-DOTA-DUNP19, $[^{225}Ac]$DUNP), an alpha-particle emitting radiometal (10 day half-life).

A tissue biodistribution study can be conducted in SCID mice bearing subcutaneous (s.c.) SAOS2, SAOS2$^{LRRC15-null}$ (CRISPR edited LRRC15) and U20S osteosarcoma tumor xenografts expressing high, null and low levels of tumor cell associated LRRC15, respectively. Uptake can be evaluated in a syngeneic pancreatic adenocarcinoma (PDAC) model with avid stromal specific expression of LRRC15 in the tumor. This PDAC model is generated by s.c. inoculation of KPP14388 cells (derived from a Kras$^{G12D}$;p16/p19$^{fl/fl}$;Pdx1-Cre PDAC GEM) in black 6 (BL/6) mice. Tumor models (n=5 per time-point) will be euthanized at 4, 24, 72, 120 and 240 hours post injection (i.v.) of the radionuclide labeled DUNP19 compound of interest. Percent activity per gram (% IA/g) will be calculated in harvested organs and tissues (specifically; tumor, blood, muscle, intestines, liver, spleen, bone marrow, bone, kidney, bladder, lungs, heart, brain and salivary glands).

It is anticipated that $[^{89}Zr]$DUNP19, $[^{177}Lu]$DUNP and $[^{225}Ac]$DUNP would show similar biodistribution characteristics. It is also expected that tumor uptake will correlate to amount of LRRC15 expression.

Macro- and small-scale dosimetry. Results from biodistributions can be utilized for pharmacokinetic/pharmacodynamic (PK/PD) studies, which will help to determine the optimal activity of $[^{89}Zr]$DUNP19, $[^{225}Ac]$DUNP19 and $[^{177}Lu]$DUNP19 to achieve maximal tumoral uptake compared to other organs. Mean absorbed dose can be calculated using a MIRD-scheme with mouse-specific S-factors. A version of the MOBY phantom can be applied for calculation of organ/tumor S-factors relevant for the utilized animal model. Actual organ sizes can be used as input for the S-value calculations using the Monte Carlo package MCNP6. The time-integrated activity coefficient can be calculated by least-square-fitting the biokinetic data to bi-exponential curves. Normal-organ radiation absorbed doses and the effective dose for respective LRRC15 targeting radiopharmaceutical in humans can be estimated based on measured time-activity data in mice.

PET images (nanoScan PET/CT, Mediso) can be reconstructed using the Tera-Tomo™ three-dimensional (3D) PET image reconstruction with the iterative reconstruction algorithm Ordered Subset Expectation Maximum (OSEM) into an image volume with a 0.3 mm$^3$ voxel size. Manually drawn 3-dimensional ROIs can be used to determine the maximum and mean % IA/g (decay corrected to the time of injection) in various tissues. Images can be analyzed using VivoQuant imaging software (InviCRO, USA). SUV data can be analyzed by using the unpaired, two-tailed Student's t-test, with differences at the 95% confidence level (P<0.05) regarded as statistically significant. Statistical computation can be conducted using STATA and/or Prism (GraphPad).

Digital autoradiography of xenograft cryosections can be performed using a Biomolex 700 Imager (Biomolex AS, Oslo, Norway). Rendered images can be analyzed using IDL 8.5 (Exelis VIS, Harris Corporation) and ImageJ. The absorbed-dose rate distribution can be calculated using a dose point kernel (DPK) acquired by Monte Carlo simulation. Correlation between specific uptake or absorbed dose rate and cellular senescence and/or DNA-repair can be retrieved by comparing three to six ROIs (each 1.3±1.1 mm$^2$) on the autoradiographic image with identical ROIs in the correlating area on the adjacent sa-β-gal and/or H2AX stained slide. The intensity of staining per nuclear area in these images can be determined using ImageJ (Immunoratio plugin). Non-parametric Spearman correlation (IBM SPSS Statistics v.23) can be utilized to study association between absorbed dose and biomarkers.

Radiochemistry. Immuno-therapeutics can be constructed by conjugating DUNP19 with chelator DOTA prior to labeling with radionuclides $^{225}$Ac or $^{177}$Lu using previously published "one-step" protocols. Utilizing a previously evaluated method, [$^{89}$Zr]DUNP19 can be functionalized with chelator DFO B prior to labeling with the radionuclide. The immunoreactive fraction of the radio-theranostic formulations can be evaluated prior to in vivo experiments by an in vitro assay measuring specific cellular association in stably LRRC15 transfected 293T cells.

EXAMPLE 3

Non-Invasive Imaging of Response to Pharmacological Modulation of the TGF-β Receptor Pathway There are currently no non-invasive molecular biomarkers applicable for assessing tumor associated TGF-β activity. Consequently, monitoring pharmacological TGF-β inhibition and identification of optimal tumor-specific dose is challenging. In this example, the utilization of [$^{89}$Zr]DUNP for non-invasive detection and quantification of tumor associated LRRC15 as a marker for downstream TGF-β activity is examined.

Whether [$^{89}$Zr]DUNP can reliably detect TGF-β associated increase of LRRC15 expression will be investigated. SCID and BL/6 mice bearing U20S osteosarcoma and KPP14388 (PDAC) s.c. tumors, respectively, will receive TGF-β1 activation by intratumoral (i.t) injections of TSP-1-derived TGF-β1-activating peptide according to previously published protocols. [$^{89}$Zr]DUNP can be administered 10 days post-manipulation and PET/CT studies can be conducted at 24, 72 and 120 hours post intravenous administration. Uptake in TGF-β stimulated tumors (n=5) can be compared to U20S tumors (n=5) treated with an inactive 'scrambled' peptide. Tissues and tumors will be harvested and % IA/g will be assessed and correlated to values obtained by PET at the last time point.

Next, whether inhibition of the TGF-β receptor by galunisertib (LY2157299) can be detected by in vivo [$^{89}$Zr]DUNP LRRC15-PET/CT imaging will be examined. U20S and KPP14388 s.c. xenografts will be randomized into groups receiving galunisertib at 37.5 or 75 mg/kg administered twice daily by oral gavage, corresponding to 50% and 100% inhibition, or vehicle. [$^{89}$Zr]DUNP can be administered i.v 24 hours after galunisertib or vehicle treatment. LRRC15-PET/CT imaging and tissue biodistribution studies can be conducted as described above.

It is expected that [$^{89}$Zr]DUNP localization will be significantly higher in xenografts exposed to TGF-β activation compared to control, while uptake will be significantly lower and dose dependent in galunisertib treated mice. In summary, it is anticipated that these experiments will support the hypothesis that [$^{89}$Zr]DUNP can faithfully reflect intratumoral TGF-β signaling.

EXAMPLE 4

Efficacies of Low- vs. High-LET LRRC15 RIT

This example evaluates efficacies of low- vs. high-LET LRRC15 radioimmunotherapy (RIT) in animal models with target expression in malignant cells. Treatment efficacies and radio-biological effects of LRRC15-targeted RIT with different linear energy transfer (LET) will be evaluated. In addition, dose-response and therapeutic impact of intratumoral dose deposition in malignant cells as compared to stromal cell compartments will be investigated. In one embodiment, [$^{225}$Ac]DUNP19 and [$^{177}$Lu]DUNP19 represent high-LET and low-LET LRRC15 RIT, respectively. Therapeutic dose-response effects can be assessed in s.c. tumor models utilized in previous biodistribution studies. Specifically, mice with SAOS2, SAOS2$^{LRRC15-null}$, U20S or KPP14388 will receive single injection of [$^{225}$Ac]hu-DUNP19 (100 μCi or 300 μCi) or [$^{177}$Lu]huDUNP19 (120 μCi or 480 μCi). This set of tumors (n=10 per treatment, 4 models, 2 compounds, 2 doses; 10×4×2×2=160) will allow us to identify alterations generated by specific targeting and those related to passive bystander effects, such as enhanced permeability and retention (EPR). Serial tumor volumes can be obtained by caliper 3 times per week.

Next, plausible radiobiological effects in tumor cells caused by cross-fire irradiation from depositions of [$^{225}$Ac] DUNP19 or [$^{177}$Lu]DUNP19 in the neighboring stromal cells will be investigated. Together with results from the experiments above, the outcome of this study will demonstrate whether the long range effect of low-LET radionuclides on neighboring tumor cells and the short range high-LET radionuclide obliteration of the tumor stroma alone will generate similar anti-neoplastic effects. To evaluate this, KPP14388 s.c. tumors can be harvested at 120, 240 hrs. and approximately 30 days (depending on therapeutic effect) after injection of [$^{225}$Ac]huDUNP19 (100 μCi and 300 μCi) or [$^{177}$Lu]huDUNP19 (120 μCi and 480 μCi) (n=3 per treatment, 1 model, 2 doses, 2 compounds, 3 time-points; 3×1×2×2×3=36). Sections of KPP14388 tumors can be evaluated by autoradiography while adjacent sections can be co-stained for senescence-associated β-galactosidase (sa-β-gal) and DNA repair protein H2AX.

It is anticipated that both low and high-LET LRRC15-RIT will result in specific and effective eradication of the tumor stoma, generating anti-neoplastic effects through acute microenvironmental changes, exhaustion of paracrine support and increased susceptibility to the intrinsic immune system. Although utilization of low-LET LRRC15-RIT may result in less efficient obliteration of the stroma, cross-fire effects from the long range may lead to valuable destruction of the nearby tumor cells.

EXAMPLE 5

DUNP19 Radioconiugates In Vivo

Figures 4A, 4B, 4C, 4D:
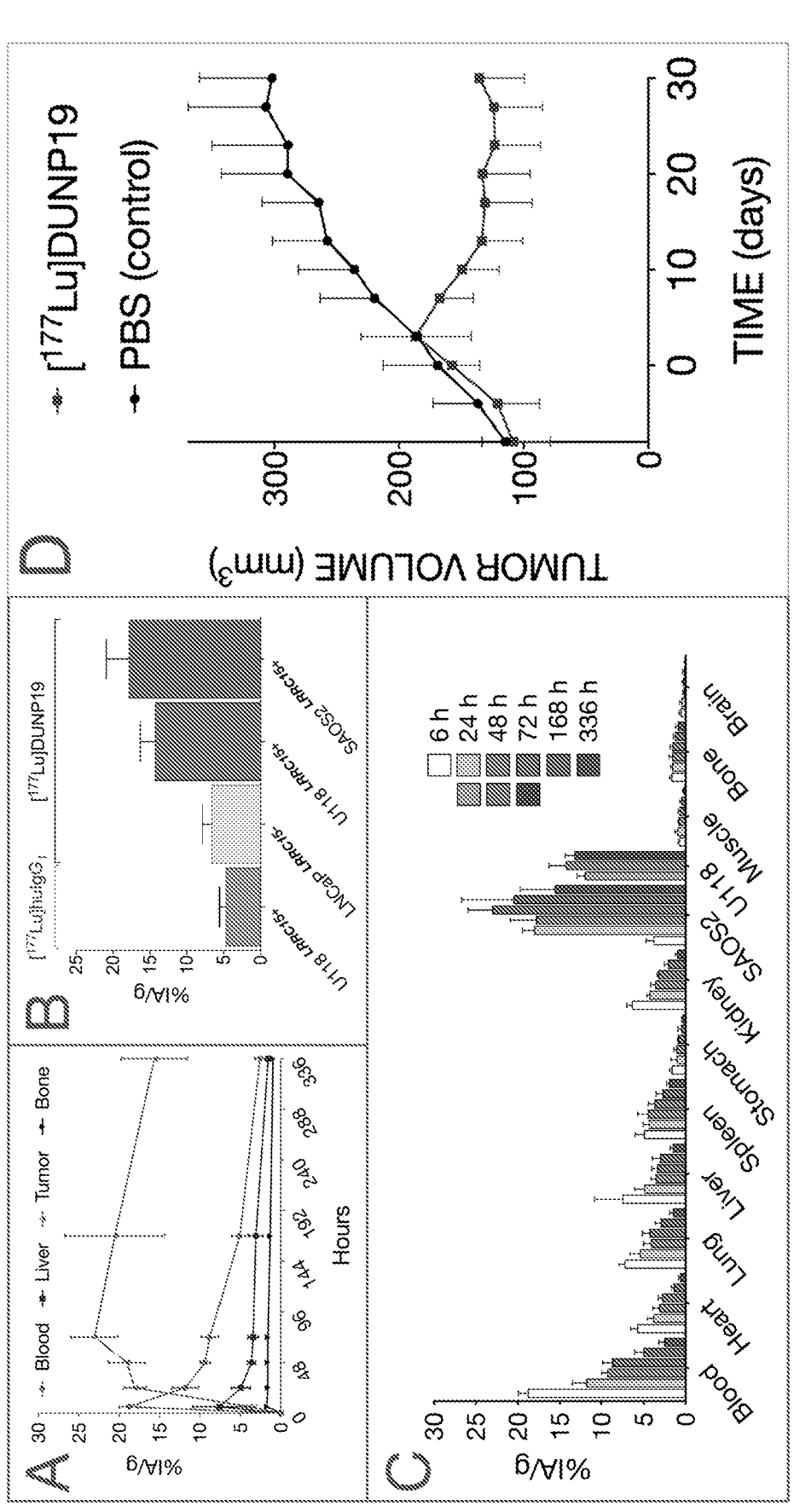
FIGS. 4A-4D show in vivo evaluation of [$^{177}$Lu] DUNP19.

This example shows intravenously (i.v.) administered Lutetium-177 labeled DUNP19 ([$^{177}$Lu]DUNP19) displayed specific and effective uptake in subcutaneous (s.c.) OS (SAOS2) models. Accumulation in normal tissues was very low and target-to-normal tissue ratios rapidly increased throughout the observed 2 weeks (see FIGS. 4A, 4C). Compared to SAOS2 models, uptake of [$^{177}$Lu]DUNP19 in s.c. U118 GBM models resulted in lower tumor specific accumulation, compatible with LRRC15 expression levels. In both models, tumors showed the highest uptake of [$^{177}$Lu]DUNP19 after 24-72 hours while rapidly clearing from all other organs (FIGS. 4B-4C). A single injection of [$^{177}$Lu]DUNP19 resulted in robust therapeutic anti-tumor effects (FIG. 4D).

Figures 5A, 5B, 5C:
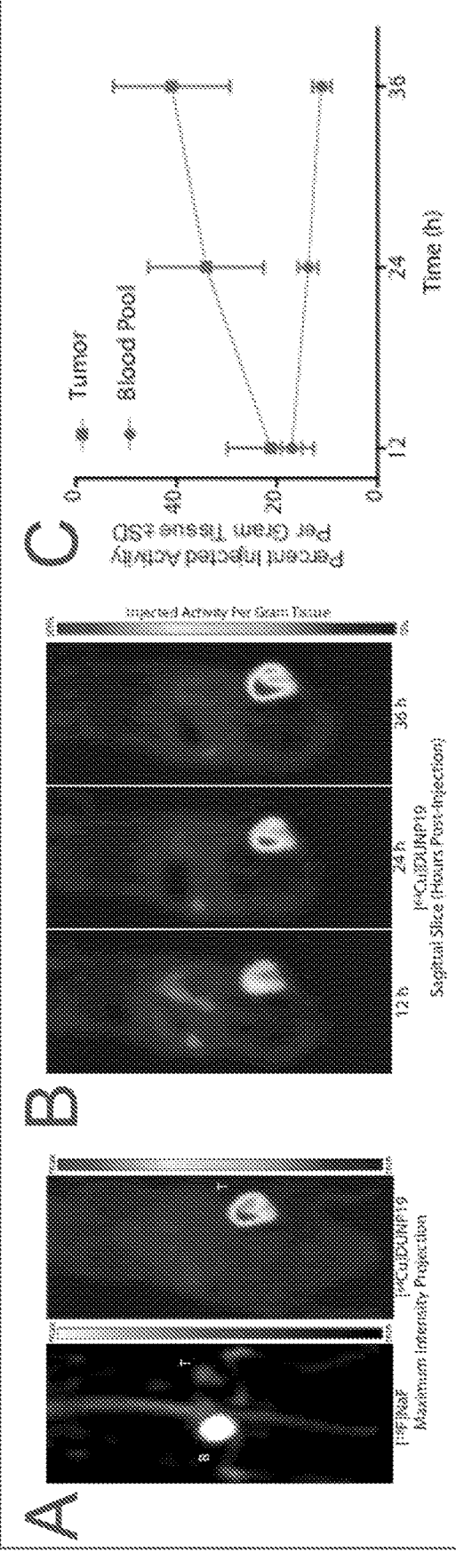
FIGS. 5A-5C show LRRC15-targeted imaging of [$^{64}$Cu] DUNP19 in s.c. OS model.

The possibility of using DUNP19 for LRRC15-targeted PET was further investigated. To explore this potential application, DUNP19 was labeled with a positron emitting radionuclide Copper-64 ([$^{64}$Cu]DUNP19). In vivo kinetics and targeting performance of [$^{64}$Cu]DUNP19 was evaluated in LRRC15 expressing osteosarcoma s.c. tumors (SAOS2). Results demonstrated highly specific uptake with excellent tumor to background ratio (FIGS. 5A-5C). Together with data based on other derivatives (e.g. [$^{177}$Lu]DUNP19, [AF594]DUNP19 and DUNP19-LF), DUNP19 clearly demonstrates impressive versatility as a therapeutic and diagnostic pharmacological agent.

Figure 6:
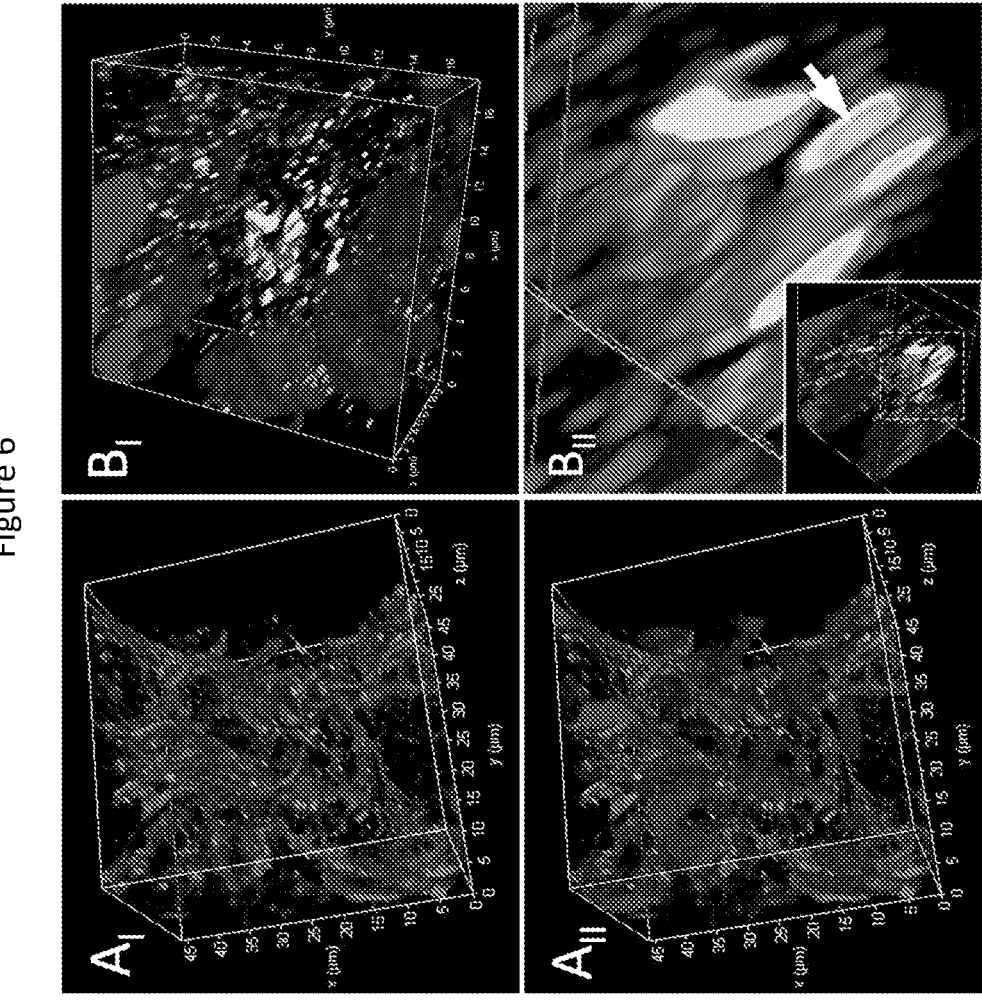
FIG. 6 show intracellular accumulation of DUNP19-LRRC15. Whole s.c. SAOS2 tumors were harvested 72 hours after i.v. injection of [AF594]DUNP19. 50 um frozen tumor sections were imaged by confocal microscopy (Leica TCS-SP5). To visualize the subcellular localization of DUNP19 (green), sections were co-stained for DNA (blue) and/or actin (red) (panels A$_I$-A$_{II}$) or DNA (blue) and LAMP1 (yellow) (panels B$_I$-B$_{II}$). These images clearly show that DUNP19 is in the cellular cytoplasm and co-localized in lysosomal compartments (see panel B$_{II}$, white arrow).

Internalization of DUNP19 into target cells in vivo after systemic administration was confirmed by confocal microscopy imaging (Leica TCS-SP5). Specifically, 50 µm cryosections of SAOS2 s.c. tumors that were harvested from animals 72 hours after i.v. administration of fluorophore AlexaFluor-594 labeled DUNP19 ([AF594]DUNP19) were imaged. To facilitate anatomical localization of [AF594]DUNP19 in relation to subcellular compartments, 50 µm sections of snap-frozen OCT-fixed blocks were co-stained for DNA (dapi, blue) and actin ([AF647]phalloidin, red), or lysosomal compartments ([AF488]LAMP1, yellow) (FIG. 6). The confocal images clearly demonstrated a majority of [AF594]DUNP19 was in the cytoplasm of the tumor cells, which is in full concordance with the in vitro results.

EXAMPLE 6

Biomarker for TGF-β Signaling

Figure 7:
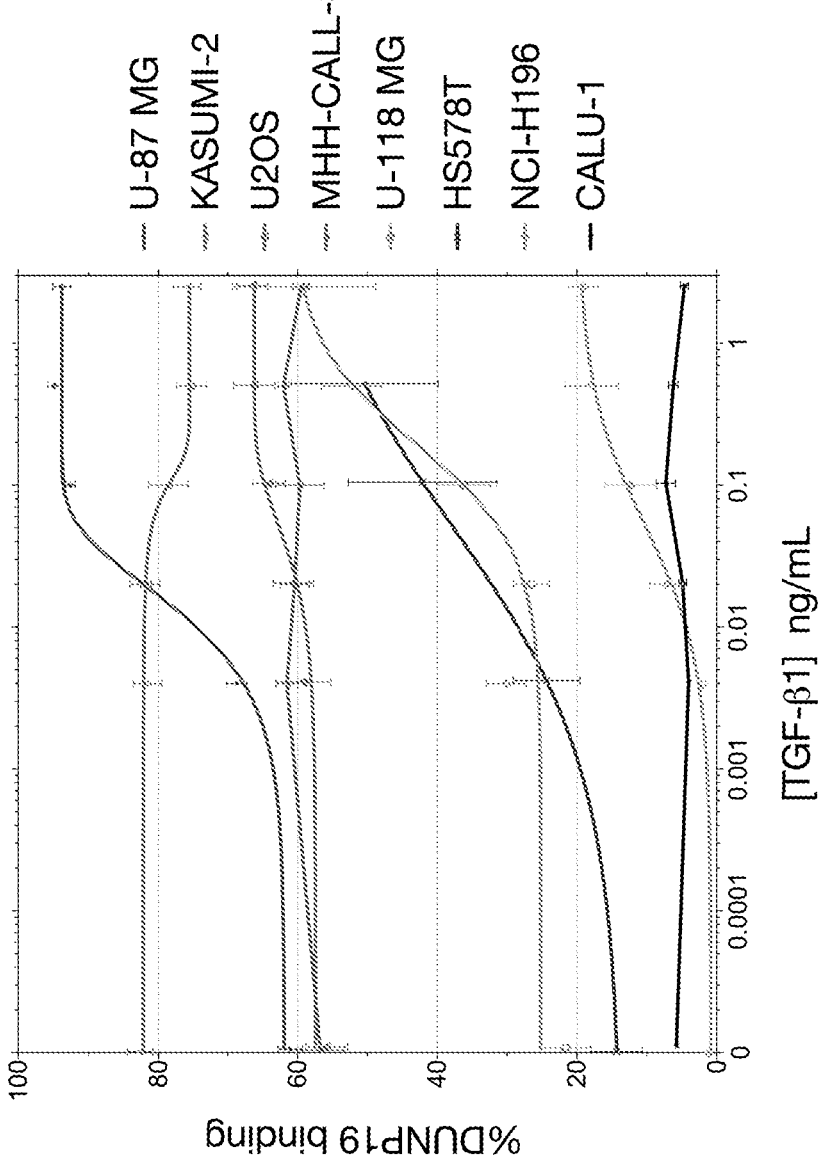
FIG. 7 shows TGF-β induced expression of LRRC15 in different cell lines.

Studies in mesenchymal stem cells (MSCs) have demonstrated that stimulation with super physiological levels of TGF-β results in induction of LRRC15 expression. Surpris-ingly, evaluation in multiple LRRC15 expressing cancer cells showed that transcriptional response to TGF-β is cell line dependent and dichotomous; induction occurs faster and at much lower levels than MSCs, or not at all. Although induced expression was noted in a majority of the cell lines, complete resistance without any induction in baseline LRRC15 level was also noted, even at high TGF-β levels (FIG. 7). Interestingly, in all cell lines tested, inhibition of TGF-β receptor effectively decreased LRRC15. Absence of induction was noted in cells derived from less aggressive disease. Thus, LRRC15 regulation may be linked to TGF-β's contrasting roles of promoting aggressive tumor growth while suppressing primary cancer. Taken together with previously reported data showing that LRRC15 expression is predominantly found in aggressive cancer forms, it is very highly likely that LRRC15-directed PET will provide clinicians with important diagnostic information.

EXAMPLE 7

Utilization of DUNP19 for Antibody Dependent
Cellular Cytotoxicity

A low fucose variant of DUNP19 (DUNP19-LF) was constructed to evaluate the possibility of treating LRRC15-expressing tumors by directing effector cells to recognize cell surface bound DUNP19-LF. Specifically, LRRC15-directed ADCC was studied in cell lines derived from hematological malignances (B-cell acute lymphoblastic leukemia lines Kasumi-2 and MHH-Call-3) and a solid tumor (Osteosarcoma, SAOS2). The target cells were labeled with 1 uM CFDA-SE and plated at 0.01×10$^6$ cells per well in a 96-well plate. Serial dilutions of 0-100 ng/mL of DUNP19-LF or non-specific low fucose isotype control (IgG1-LF) were added to target cells and incubated for 40 minutes at 37 degrees before the addition of effector cells. NK92 transfected CD16 effector cells were activated with 100 U/mL IL-2 for 24 hours before adding to target cells at 5:1 or 10:1 effector:target cell ratios. Assay plates were then incubated for 6 hours at 37 degrees and dead cells were stained with fixable viability dye (FVD) 660. Flow cytometry was used to determine all CFDA-SE+/FVD660+ cells to identify dead target cells killed by antibody dependent cell-mediated cytotoxicity.

LRRC15-targeted ADCC using DUNP19-LF was demonstrated in the LRRC15-expressing tumor cell lines Kasumi-2 and MHH-Call-3 and solid tumor cell line Saos-2. In B cell acute lymphoblastic leukemia lines Kasumi-2 and MHH-Call-3, addition of 2 ng/mL to 8 ug/mL of anti-LRRC15 DUNP19 increased NK92-CD16 mediated cytotoxicity from 25% to 60-80%, indicating that DUNP19 can specifically direct NK92-CD16 cells to initiate ADCC in LRRC15 positive tumor lines. With the addition of isotype control antibody IgG1-LF or effector cells alone, target cell death remained below 30% and is attributable to nonspecific cytotoxicity of NK92-CD16 cells towards tumor cells. In osteosarcoma cell line SAOS2, ADCC was observed with the addition of 0.4 ng/mL to 100 ng/mL DUNP19, killing between 35-50% of SAOS2 cells. Overall target cell death in both the control and experimental groups was lower than previous ADCC assays and may be due to the varying degrees of cell viability and activation seen in the effector NK92-CD16 cell line. In summary, these results demonstrate that unlabeled DUNP19 has an impressive potential as an LRRC15 targeted immunotherapeutic compound.

What is claimed is:

1. A composition comprising
an antibody or antibody fragment that binds to leucine-rich repeat-containing protein 15 (LRRC15), comprising
a variable heavy chain having the amino acid sequence of SEQ ID NO:1, and
a variable light chain having the amino acid sequence of SEQ ID NO:2 wherein the antibody or antibody fragment is conjugated to DOTA bound to 177-Lu.

2. The composition of claim 1, wherein the antibody or antibody fragment is an antibody.

3. The composition of claim 1, wherein the antibody or antibody fragment is an antibody fragment.

4. The composition of claim 1, wherein the antibody or antibody fragment is a monoclonal antibody.

5. The composition of claim 1, wherein the antibody or antibody fragment is a monoclonal antibody fragment.

6. The composition of claim 1, wherein the antibody or antibody fragment is a humanized monoclonal antibody.

7. The composition of claim 1, wherein the antibody or antibody fragment is a humanized monoclonal antibody fragment.

8. The composition of claim 1, wherein the antibody or antibody fragment is an Fv fragment, an antigen binding fragment (Fab), a F(ab')2 fragment, or a single chain variable fragment (scFv).

9. The composition of claim 1, wherein the antibody or antibody fragment has picomolar affinity for LRRC15.

10. The composition of claim 1, wherein the antibody or antibody fragment is internalized by LRRC15-expressing cells.

11. The composition of claim 1, wherein the antibody or antibody fragment binds to a phylogenetically conserved epitope on LRRC15.

12. The composition of claim 1, wherein the antibody or antibody fragment is an afucosylated antibody.

13. The composition of claim 1, wherein the antibody or antibody fragment is a low-fucose antibody.

14. The composition of claim 1, wherein the composition is formulated for intravenous administration.

15. The composition of claim 1, wherein the antibody or antibody fragment is a bispecific antibody.

16. The composition of claim 15, wherein the bispecific antibody comprises specificity for binding to TGF-β.

17. The composition of claim 16, wherein the TGF-β-binding portion comprises a variable heavy chain having the sequence of SEQ ID NO:3 and a variable light chain having the sequence of SEQ ID NO:4.

18. The composition of claim 1, wherein the antibody or antibody fragment is a trispecific antibody.

19. The composition of claim 18, wherein the trispecific antibody comprises specificity for binding to TGF-β.

20. The composition of claim 19, wherein the TGF-β-binding portion comprises a variable heavy chain having the sequence of SEQ ID NO:3 and a variable light chain having the sequence of SEQ ID NO:4.

21. The composition of claim 18, wherein the trispecific antibody comprises a second LRRC15-binding portion.

22. The composition of claim 21, wherein the second LRRC15 binding portion comprises a variable heavy chain having the amino acid sequence of SEQ ID NO:1, and a variable light chain having the amino acid sequence of SEQ ID NO:2.

\* \* \* \* \*